United States Patent [19]

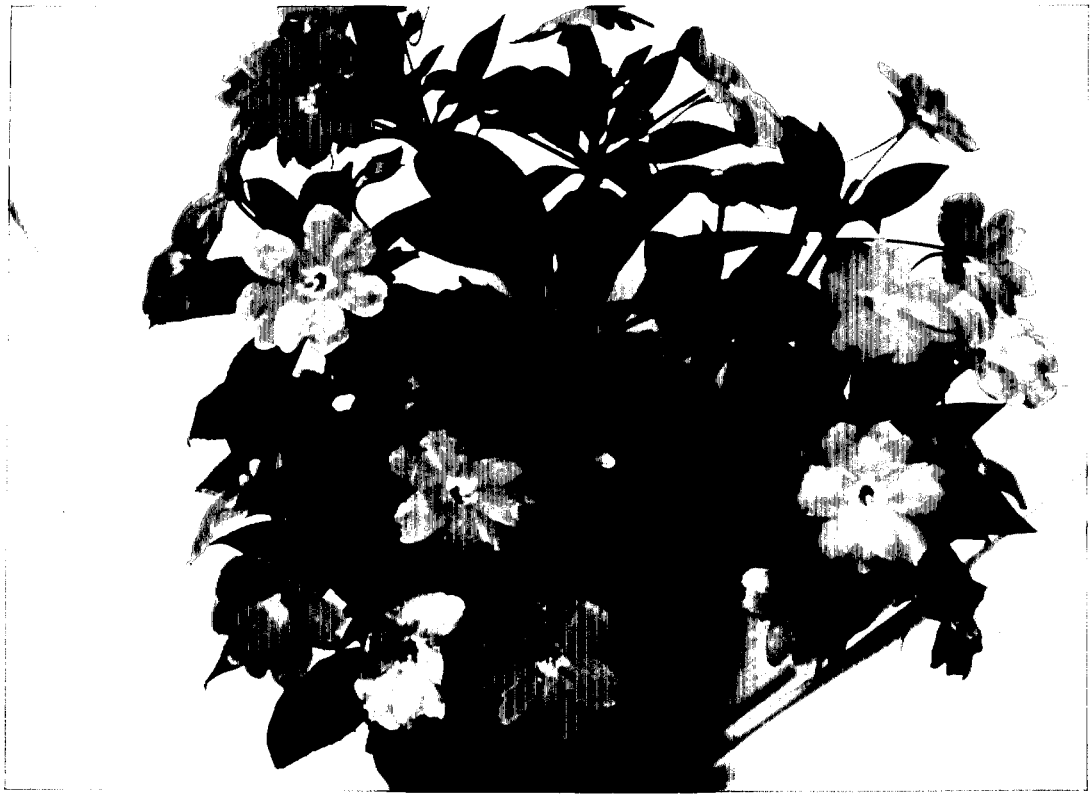

Hope

[11] Patent Number: Plant 5,563

[45] Date of Patent: Sep. 24, 1985

[54] IMPATIENS PLANT NAMED VISTA IMPATIENS NO. 37

[75] Inventor: Claude Hope, Cartago, Costa Rica

[73] Assignee: Pan American Plant Company, Parrish, Fla.

[21] Appl. No.: 566,502

[22] Filed: Dec. 29, 1983

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of impatiens plant named Vista Impatiens No. 37 characterized by its large vivid fuchsia colored flowers with a light center eye, dark green foliage, good self-branching habit, moderate rate of growth, highly floriferous and substantially continuous flower habit, and by its tall upright habit, making the cultivar suitable for bedding plants and pot plant culture.

1 Drawing Figure

The present invention relates to a new and distinctive cultivar of impatiens plant, botanically known as Impatiens, and known by the cultivar name Vista Impatiens No. 37.

The new impatiens was the result of a planned program of hybridization for the purpose of obtaining a series of plants having a wide range of colors and very large flowers derived from the New Guinea complex of species collected by the Longwood Garden Expedition of 1970. The new cultivar was selected in 1980, and was designated seedling No. 3347-1. The parents of the new cultivar are unknown at this time. Asexual reproduction by terminal or stem cuttings taken at Cartago, Costa Rica has shown that the unique features of the new cultivar are stabilized and are reproduced true to type in successive propagations.

The following characteristics distinguish the new impatiens from other cultivated impatiens of this type known and used in the floriculture industry:

1. Vista Impatiens No. 37 was selected and is principally characterized by its large (61 mm.) and vivid fuchsia colored flowers which have a light eye in the center of the flower.

2. The cultivar is highly floriferous, with flowering being continuous.

3. Foliage is dark green and provides a pleasant contrast with the flower color.

4. Exhibits good self-branching habit.

5. Rate of growth is moderate, producing in 6–8 weeks a plant 20–40 cm. tall and 35 cm. in diameter (5½" pot) when grown outdoors under full sun in spring, fall, winter and under light shade in summer in Florida.

6. Habit is tall (45–60 cm. full grown) and upright, making it ideal for bedding plants and pot plant culture.

The accompanying colored photograph illustrates the overall appearance of the new cultivar, showing the colors as true as it is reasonably possible to obtain in a colored reproduction of this type.

The following is a detailed description of my new impatiens cultivar based on plants produced under commercial practice in Cortez and Parrish, Fla. The plants were produced outdoors in full sun during fall, winter and spring months, and under light shade during the summer months. Color references are made to The Royal Horticultural Society Colour Chart except where general terms of ordinary dictionary significance are used.

Parentage: Unknown.

Propagation:

A. *Type cutting.*—Tip cuttings with 5 cm. stems.

B. *Time to initiate roots.*—10–14 days at 27° C. summer; 12–16 days at 18° C. winter.

C. *Rooting habit.*—Abundant and fibrous.

Plant description:

A. *Form.*—Tall, upright, dome-shaped.

B. *Habit of growth.*—Rate of growth moderate for this type of plant. Vegetative shoots are formed at the lower nodes and flowers at the higher nodes.

C. *Foliage description.*—Lower leaves opposite, higher leaves in whorls of 5–6. Leaves are simple. (1) Size: Average full grown leaf is 140 mm. long×49 mm. wide. Full grown leaves have petioles 45 mm. long. Young leaves have 3–9 mm. long petioles. (2) Shape: Elliptic, apex slightly acuminate, base attenuate. (3) Texture: Smooth surface, glabrous. (4) Margin: Serrulate. (5) Color, young foliage, top side green 137C, under side green 138B; mature foliage, top side green 139A, under side close to greyed green 191B. (6) Venation: Pinnate, main vein top side greyed green 193A and very slightly infused with red; underside infused with red.

Flowering description:

A. *Flowering habits.*—Very floriferous, flowers occurring progressively around the whorl of leaves. Flowers are large and single.

B. *Natural flowering season.*—Flowering is indeterminate and occurs throughout the year except for periods of high light and high temperature in Florida.

C. *Flower bud description.*—Conical, covered with 3 sepals; upper two sepals are 9 mm. long×5 mm. wide, apex acuminate. Upper sepals green slightly infused with pink at the base, lower sepal colorless infused with green at the apex and infused with pink at the base. Hollow spur is 45 mm. long when full grown, connected to lower sepal and reddish pink in color.

D. *Flowers borne.*—On peduncles 5 mm. long, tan to green in color.

E. *Quantity of flowers.*—One flower per leaf, occurring progressively around the whorl of leaves.

F. *Petals.*—(1) Shape: Top petal heart-shaped with a wide, rounded base; all other petals heart-shaped with pointed bases. (2) Color; top side red-purple 57A when opening, with a center eye that starts at red-purple 66A and fades to red-purple 57D; the main flower portion fades to between red-purple 57B and C; under side red-purple 57C. (3) Number of petals: Five. (4) Size of flowers: Top petal 25 mm. long×33 mm. wide; 2 middle petals 31 mm. long×20 mm. wide; 2 lower petals 34 mm. long×25 mm. wide. Total flower diameter is 61 mm.

G. *Reproductive organs.*—(1) Stamens: Five, with the lower stamen being shorter than the others. Stamens united in an asymmetrical tube surrounding and covering the ovary. (a) Anther shape; hooded, color cream infused with deep pink. (b) Pollen color: cream. (2) Pistels: (a) Stigma: five pointed star, colorless. (b) Styles: very short, cream in color. (c) Ovaries: 5, celled. 5–6 mm.; color green.

Disease resistance:

No general plant diseases noted. Insect problems can include the two-spotted spider mite which can cause foliar injury and thrips which can cause stunting and injury to the growing tip.

I claim:

1. A new and distinct cultivar of impatiens plant named Vista Impatiens No. 37, as described and illustrated, and characterized by its large vivid fuchsia colored flowers with a light center eye, dark green foliage, good self-branching habit, moderate rate of growth, highly floriferous and substantially continuous flower habit, and by its tall upright habit, making the cultivar suitable for bedding plants and pot plant culture.

* * * * *